(12) United States Patent
Massicotte

(10) Patent No.: US 11,413,435 B2
(45) Date of Patent: Aug. 16, 2022

(54) METHODS FOR CONSTRUCTION OF MEDICAL DEVICES CONTAINING TOROIDAL BALLOONS

(71) Applicant: J. Mathieu Massicotte, North Reading, MA (US)

(72) Inventor: J. Mathieu Massicotte, North Reading, MA (US)

( * ) Notice: Subject to any disclaimer, the term of this patent is extended or adjusted under 35 U.S.C. 154(b) by 65 days.

(21) Appl. No.: 16/387,737

(22) Filed: Apr. 18, 2019

(65) Prior Publication Data

US 2019/0321604 A1   Oct. 24, 2019

Related U.S. Application Data

(60) Provisional application No. 62/659,756, filed on Apr. 19, 2018.

(51) Int. Cl.
| | |
|---|---|
| *A61M 25/10* | (2013.01) |
| *B29C 49/18* | (2006.01) |
| *B29C 49/42* | (2006.01) |
| *B29L 31/00* | (2006.01) |

(52) U.S. Cl.
CPC .... *A61M 25/1034* (2013.01); *A61M 25/1002* (2013.01); *B29C 49/18* (2013.01); *B29C 49/4273* (2013.01); *B29K 2995/0056* (2013.01); *B29L 2031/7543* (2013.01)

(58) Field of Classification Search
CPC .......... A61M 25/1029; A61M 25/1034; A61M 25/1027; A61M 25/0119; B29C 49/18; B29C 49/04; A61B 17/3423

USPC .......................................................... 156/245
See application file for complete search history.

(56) References Cited

U.S. PATENT DOCUMENTS

| | | | | |
|---|---|---|---|---|
| 4,935,190 A | * | 6/1990 | Tennerstedt | A61M 25/1029 264/529 |
| 6,942,640 B2 | * | 9/2005 | Kokish | A61M 25/10 604/103.06 |
| 2014/0343593 A1 | * | 11/2014 | Chin | A61M 25/09041 606/194 |
| 2019/0000429 A1 | * | 1/2019 | Magana | A61B 17/3421 |

FOREIGN PATENT DOCUMENTS

| | | | | |
|---|---|---|---|---|
| EP | 0200668 A2 | * | 11/1986 | ........... A61B 17/221 |
| EP | 0937482 A2 | * | 8/1999 | ......... B29C 67/0014 |

OTHER PUBLICATIONS

"Gateway Advantage: Y-Adapter" (Available Jul. 1, 2017) <https://www.bostonscientific.com/en-US/products/accessories/gateway.html> (Year: 2017).*

* cited by examiner

*Primary Examiner* — Matthew J Daniels
*Assistant Examiner* — Hana C Page
(74) *Attorney, Agent, or Firm* — Gesmer Updegrove LLP

(57) ABSTRACT

The geometry of a toroidal balloon requires that a traditional cylindrical balloon to be rotated internally into itself and the ends of the cylinder be placed in close proximity for maximal balloon rotation and to allow an entrance port for inflation of the balloon and/or attachment to an associated medical device. Described within are various techniques for the creation of such toroidal balloons.

6 Claims, 18 Drawing Sheets

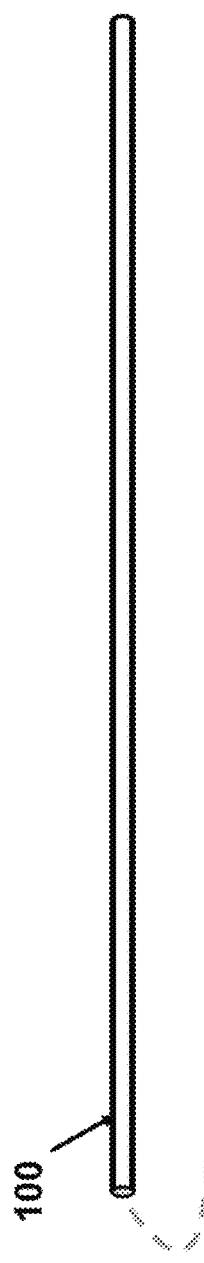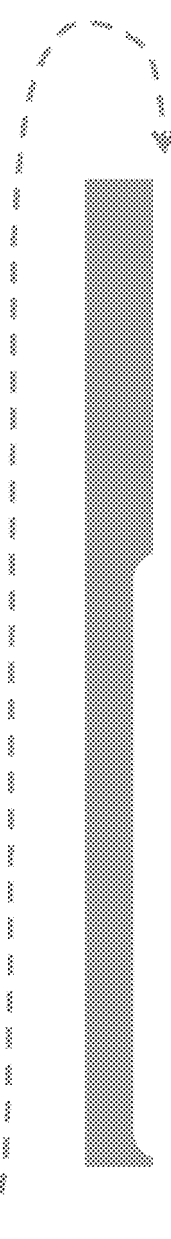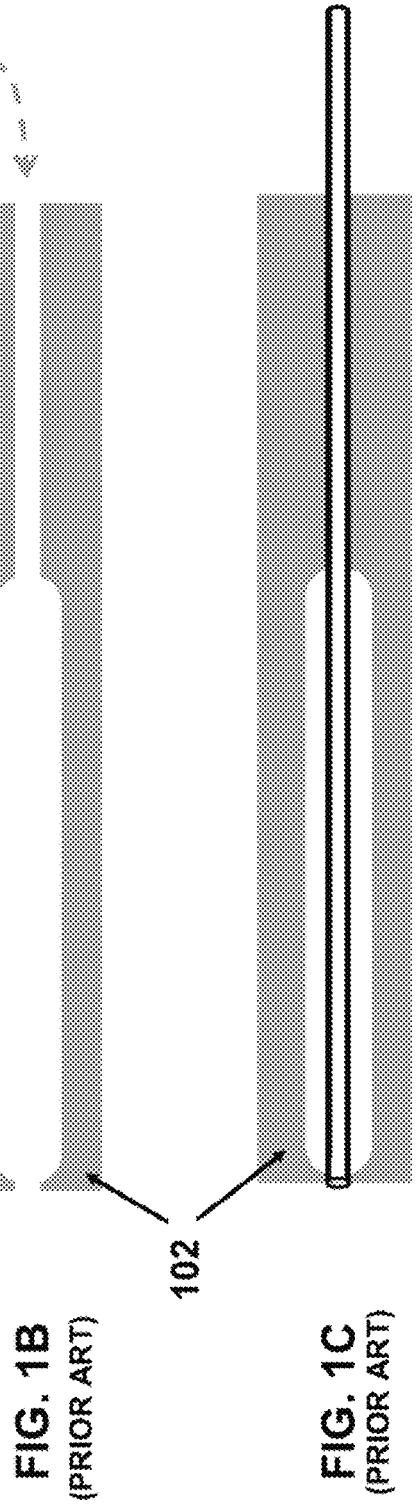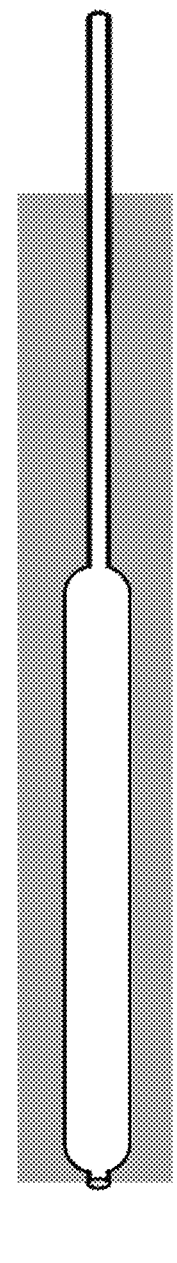
FIG. 1A (PRIOR ART)
FIG. 1B (PRIOR ART)
FIG. 1C (PRIOR ART)
FIG. 1D (PRIOR ART)
FIG. 1E (PRIOR ART)

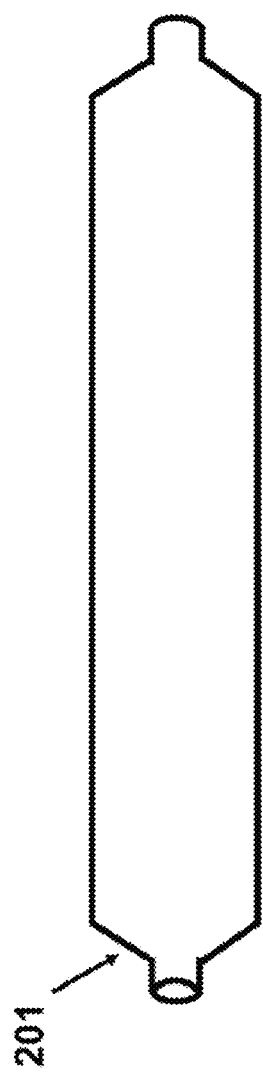
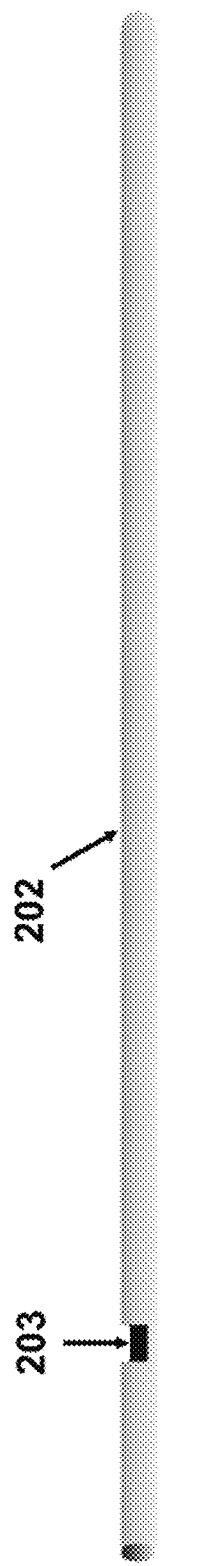
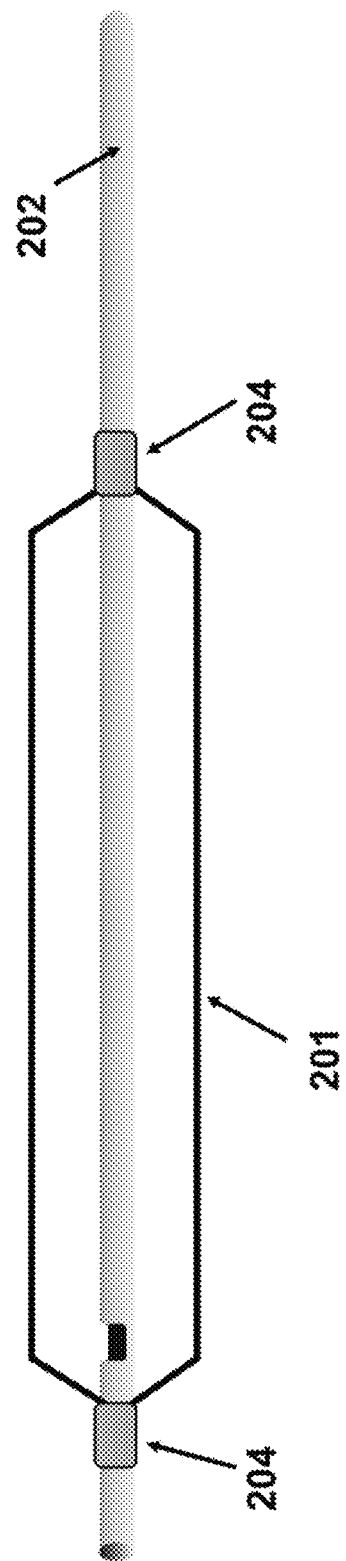
FIG. 2A
(PRIOR ART)
FIG. 2B
(PRIOR ART)
FIG. 2C
(PRIOR ART)

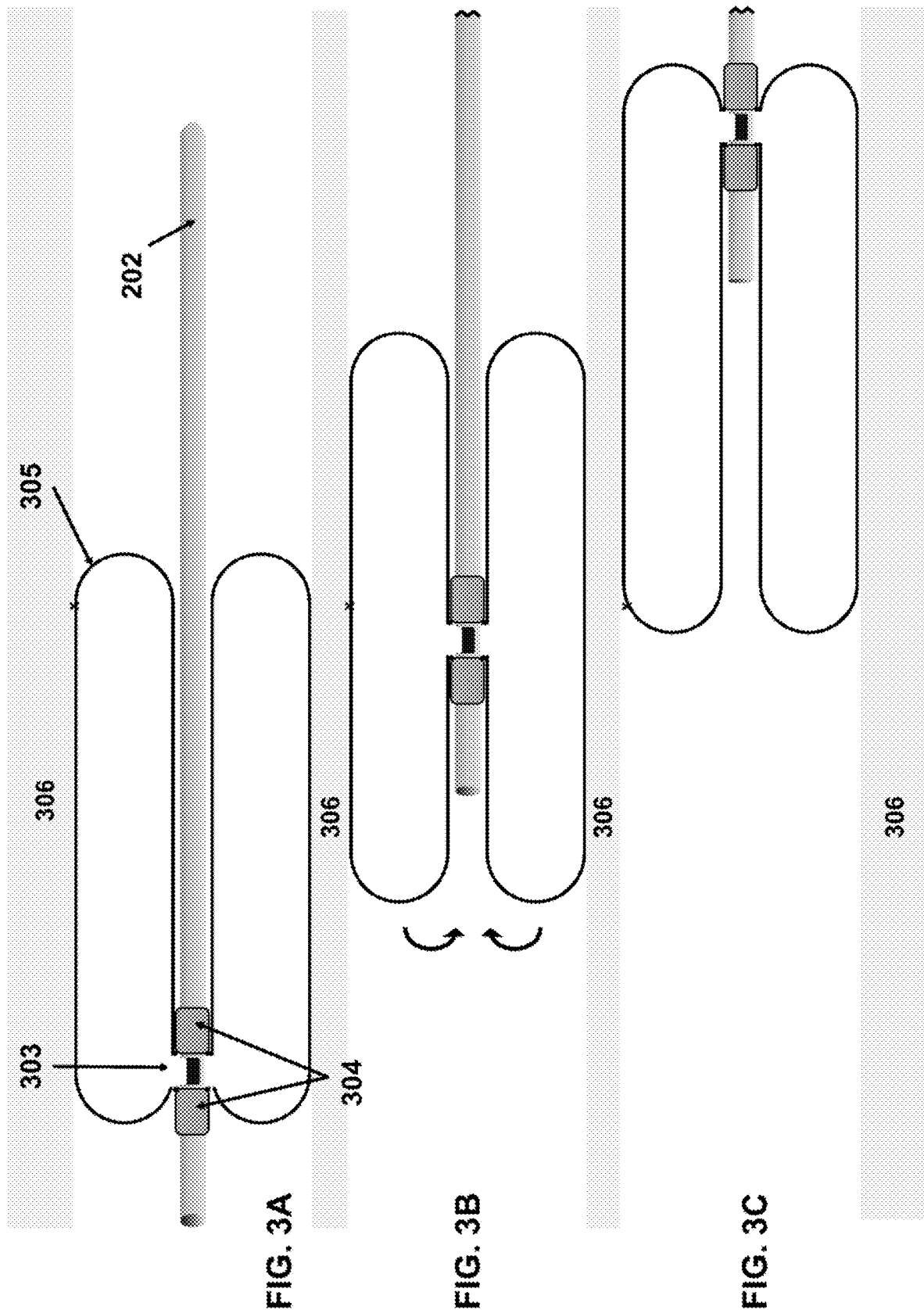

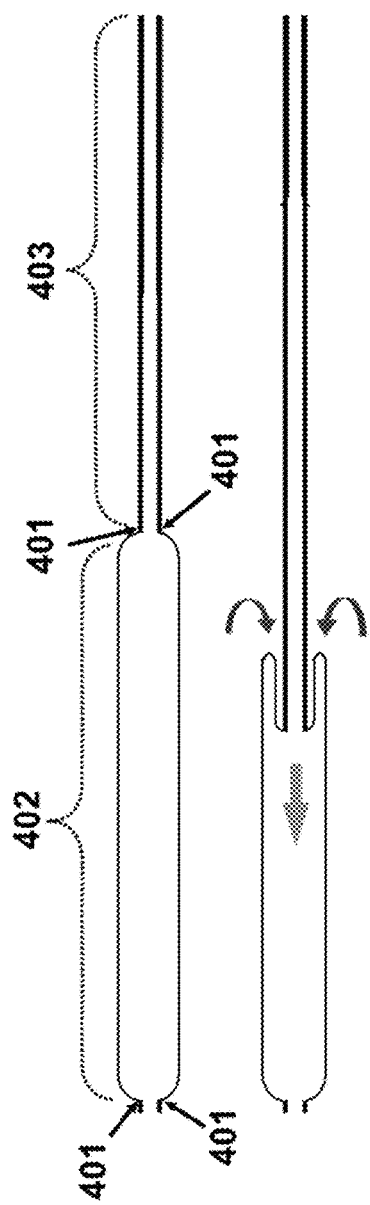
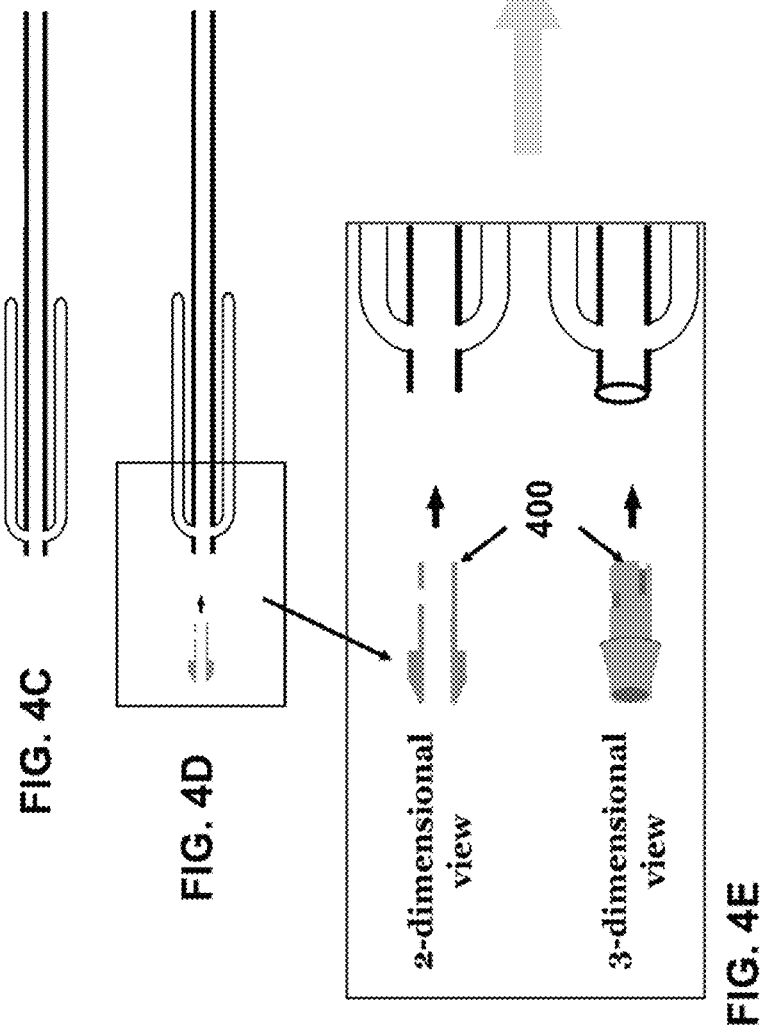
FIG. 4A
FIG. 4B
FIG. 4C
FIG. 4D
FIG. 4E
FIG. 4F

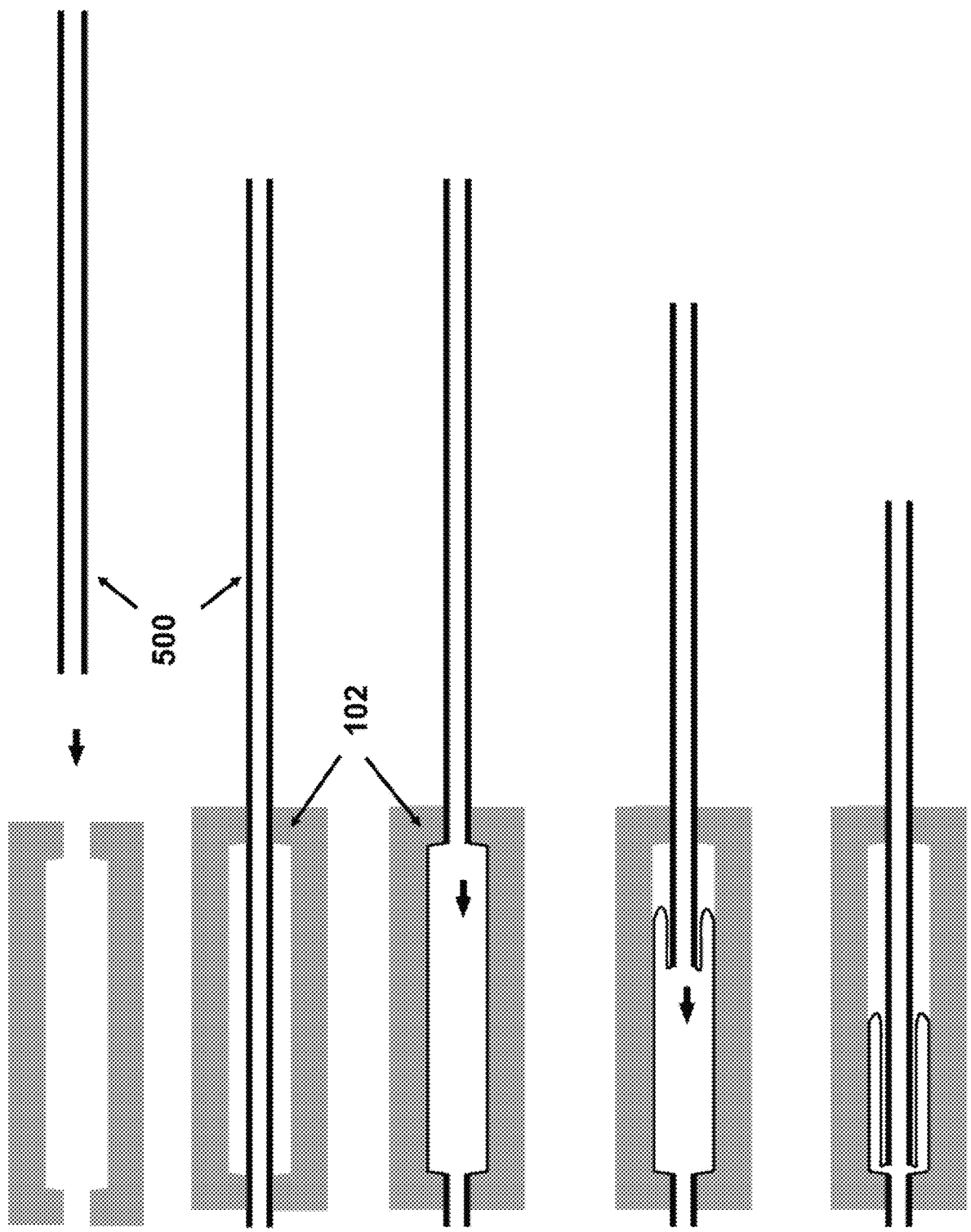

510 inserting a portion of the extruded tube in a mold cavity, the portion corresponding to the second segment, the first and third segments remaining external to the mold cavity
Step 512

→ raising a temperature within the mold cavity and inflating the second segment of the extruded tube so it conforms to a cylindrical shape of the mold cavity
Step 514

→ advancing the third segment of the extruded tube in a direction of the central axis of the second segment that is inflated in (b) and towards the first segment, the advancing done until the second segment forms a toroidal configuration surrounding the third segment
Step 516

→ sealing the first and third segments
Step 518

FIG. 5F

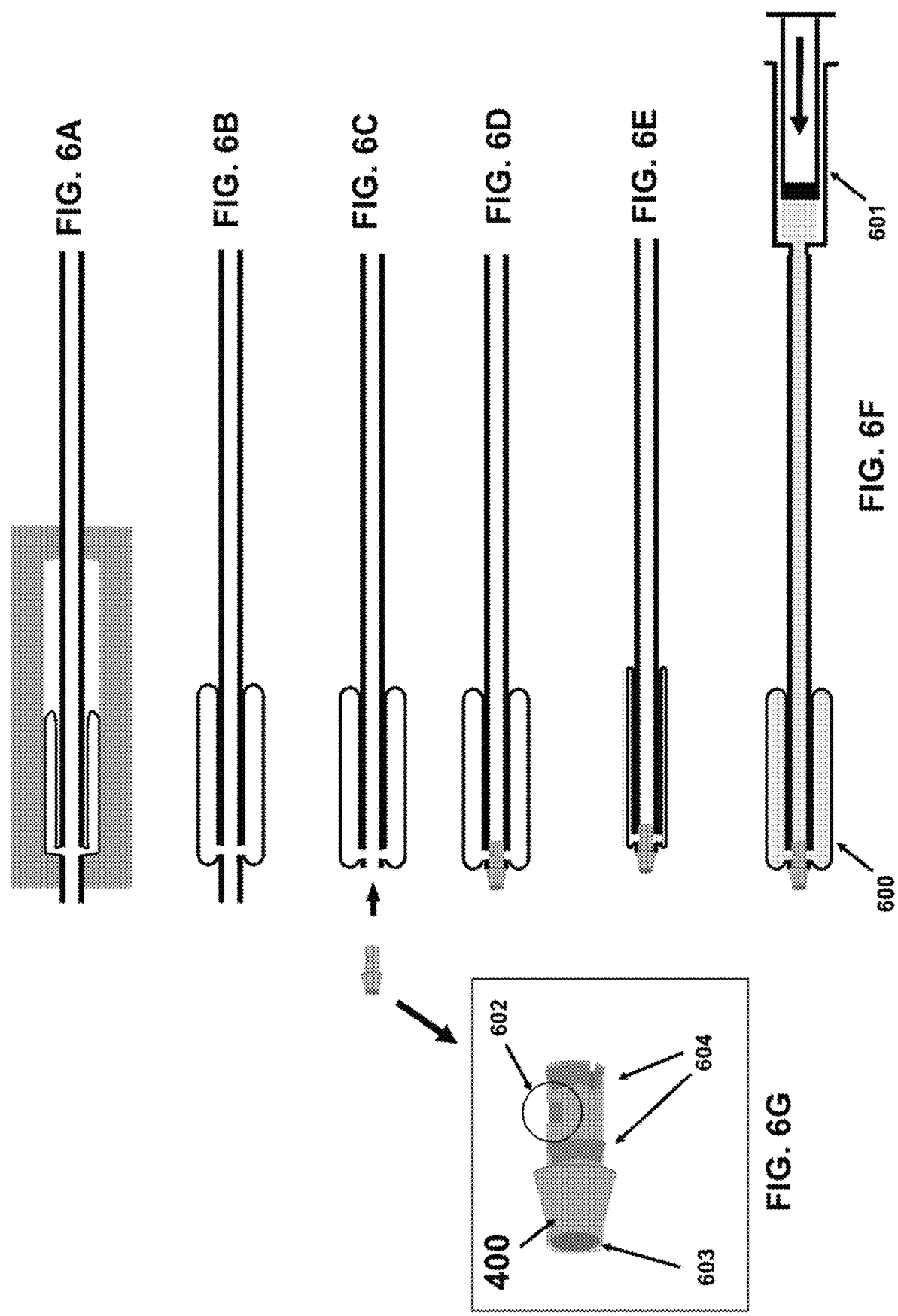

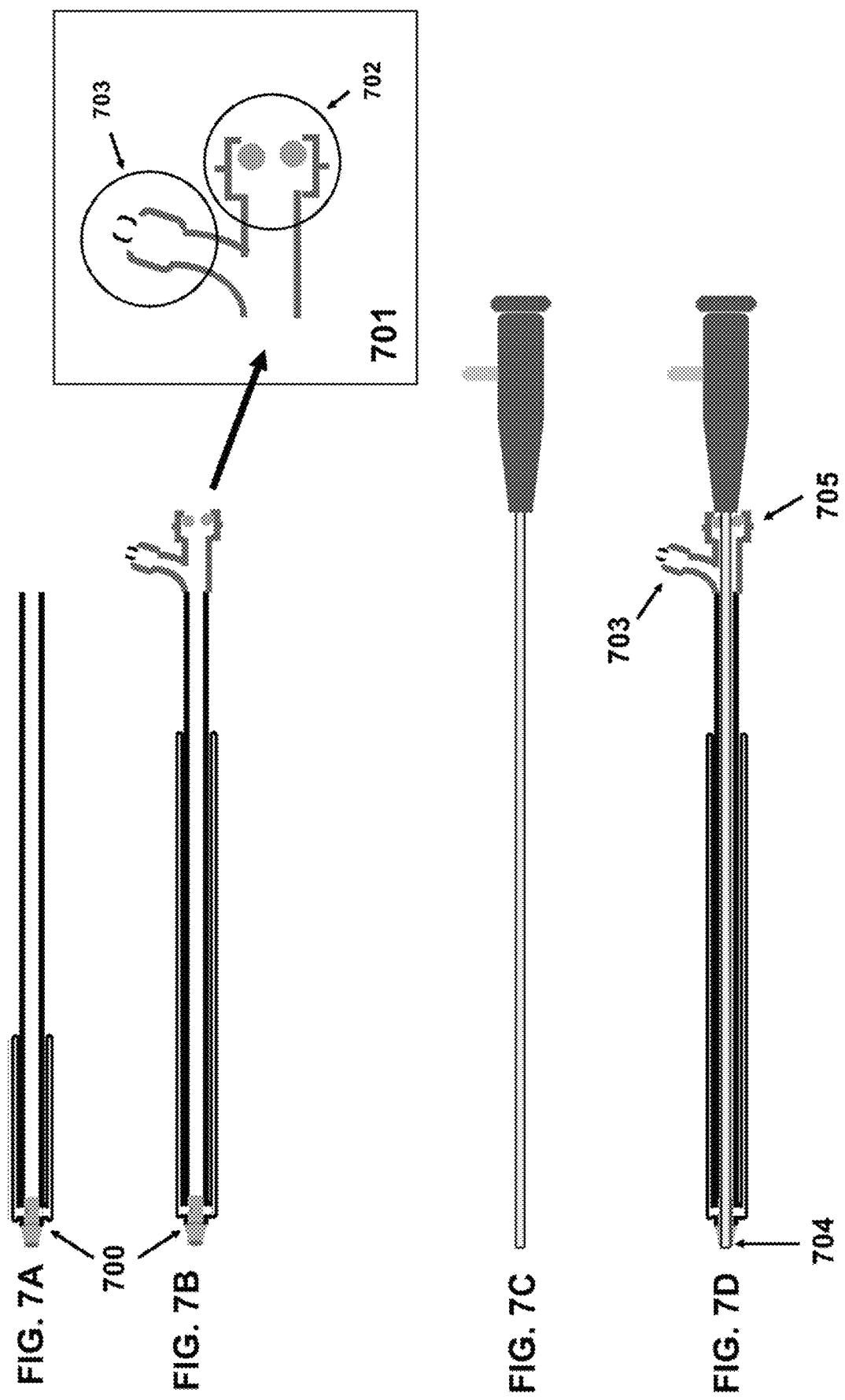

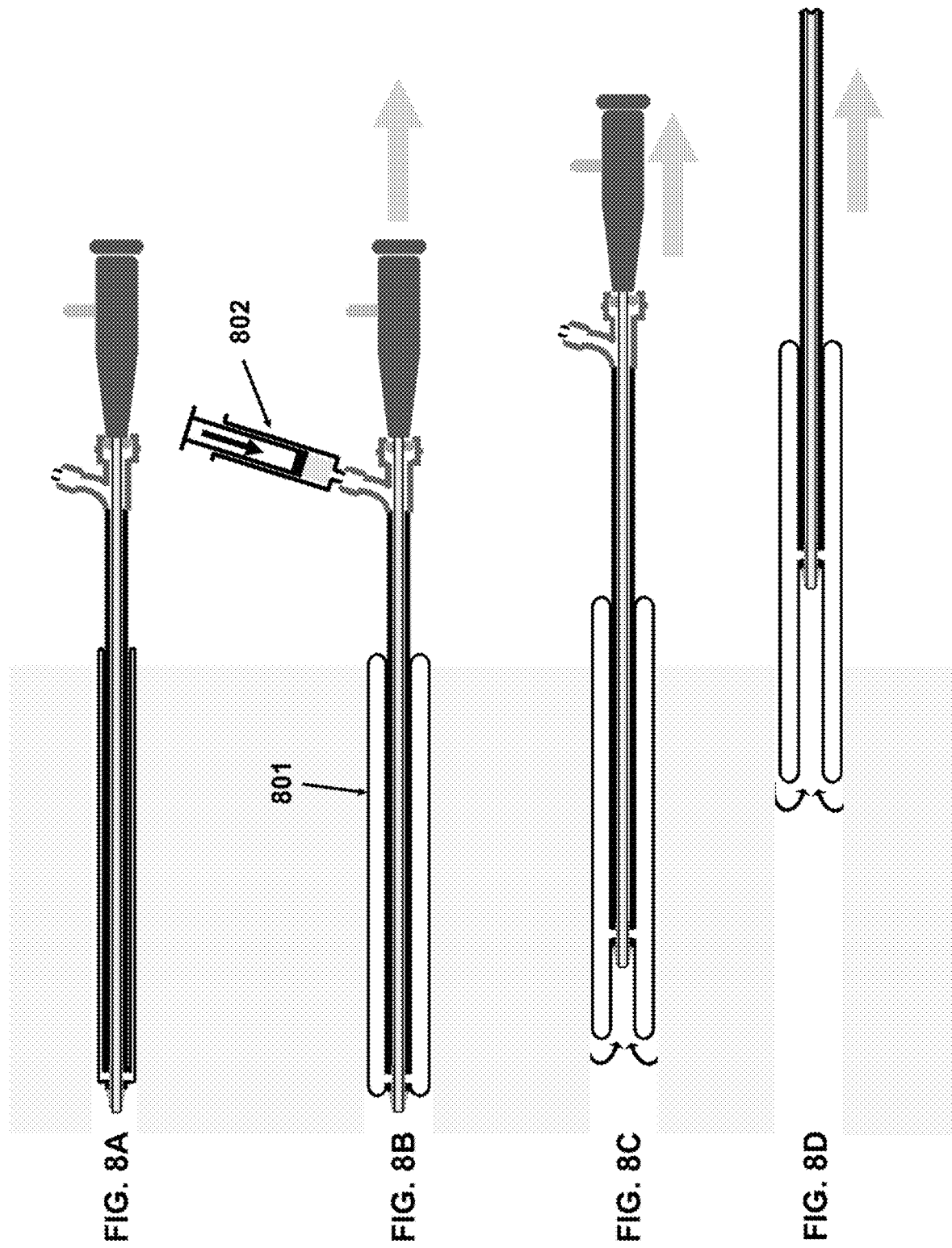

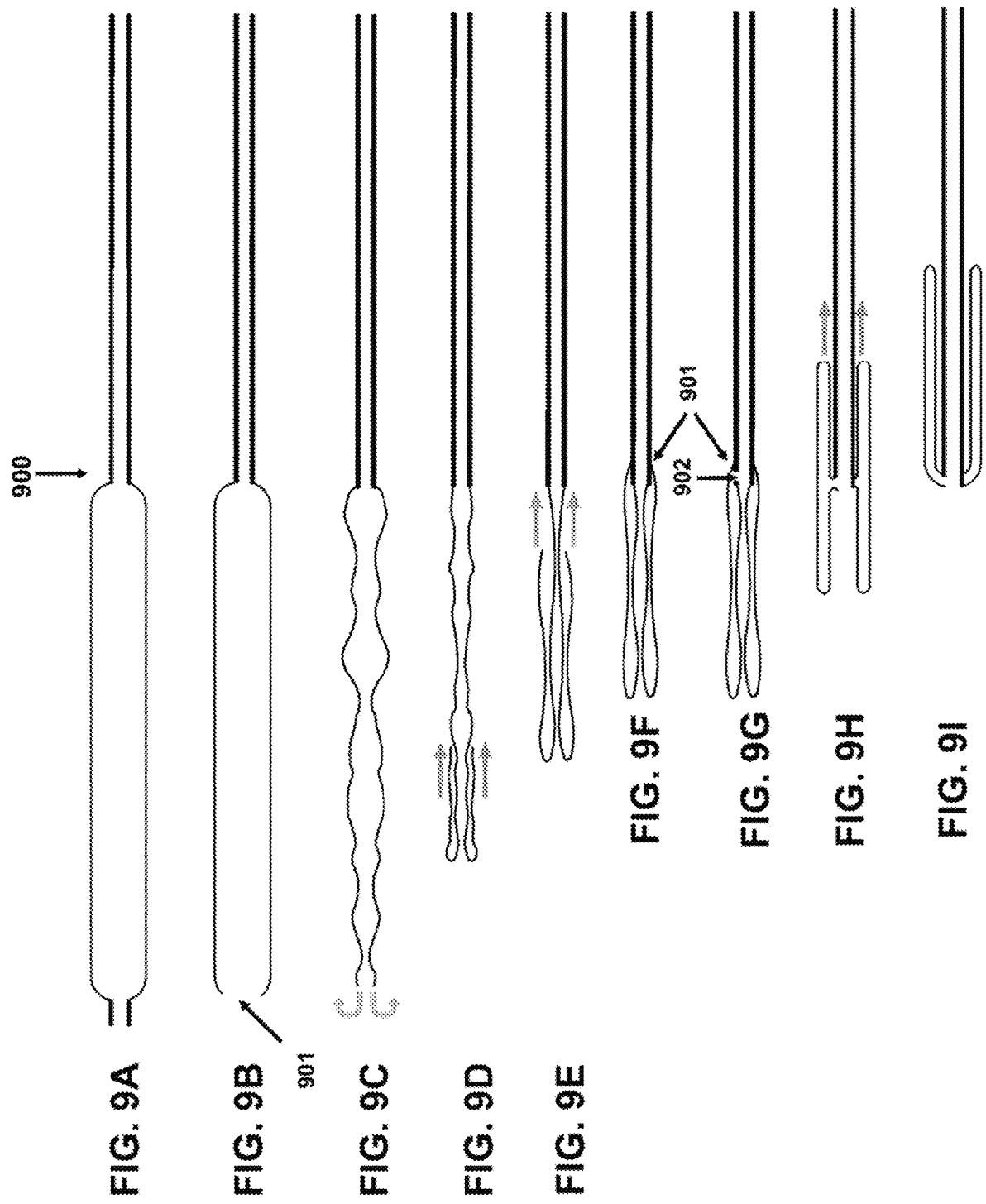

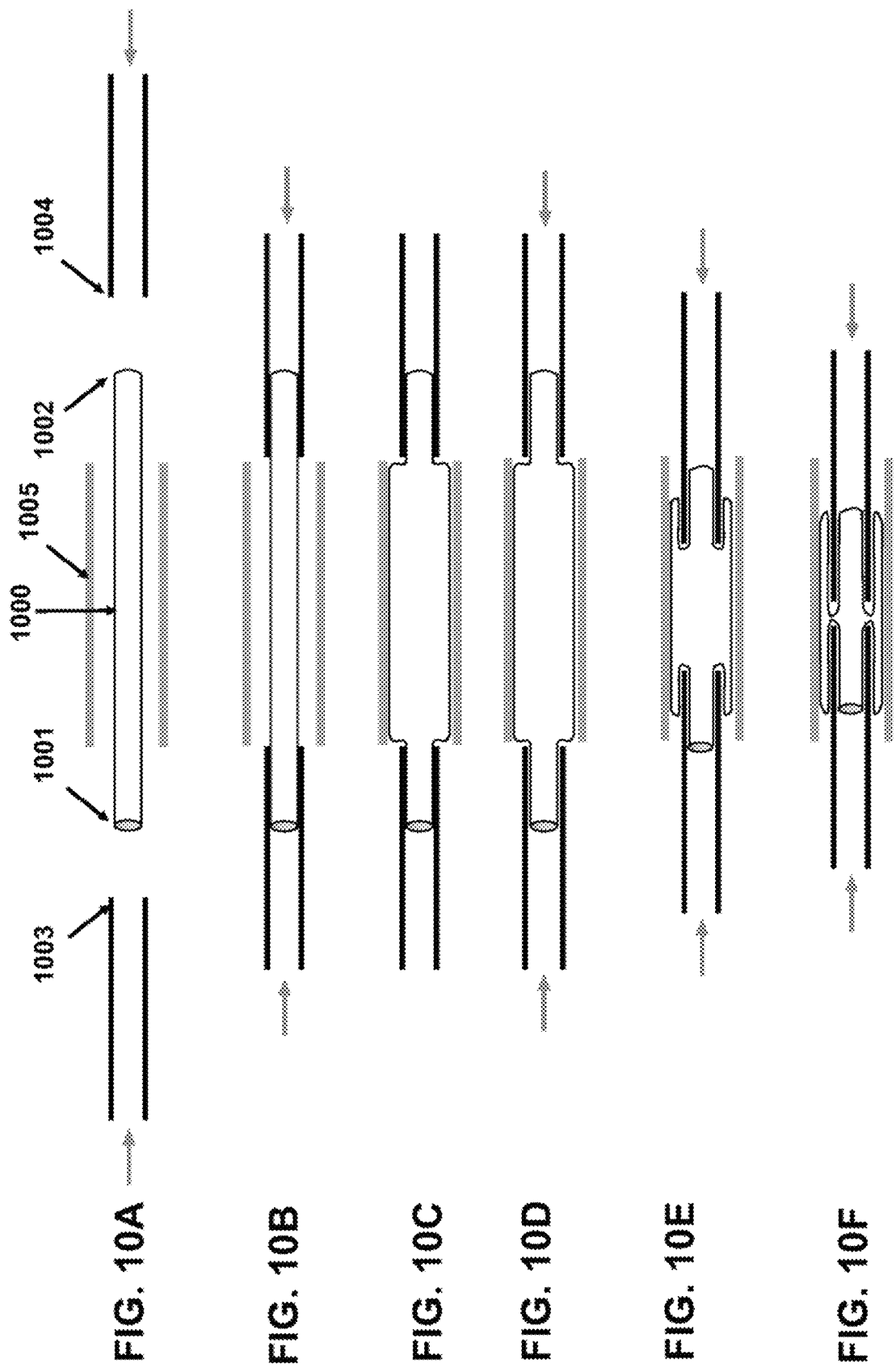

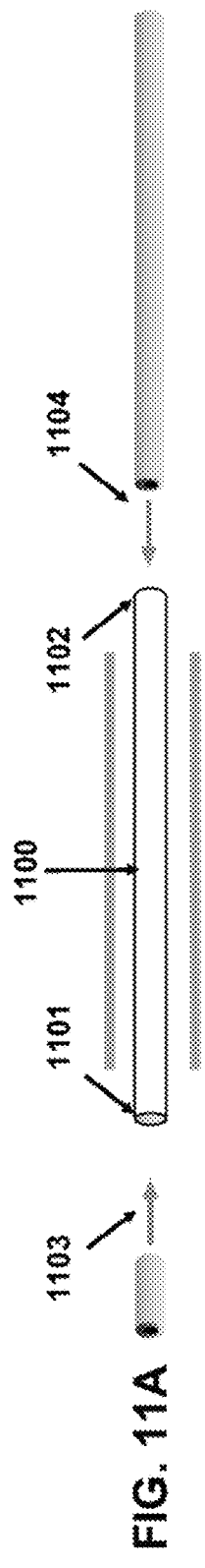
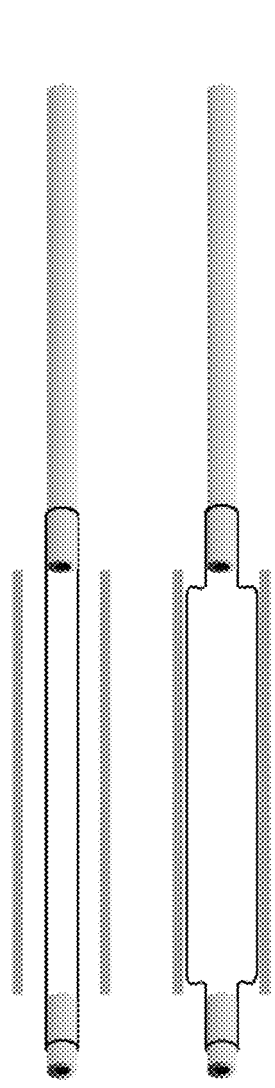
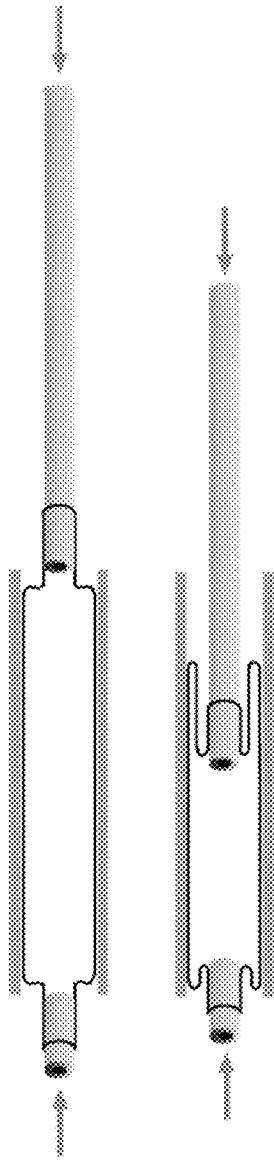
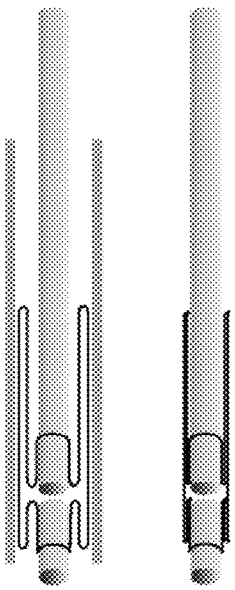
FIG. 11A  FIG. 11B  FIG. 11C  FIG. 11D  FIG. 11E  FIG. 11F  FIG. 11G

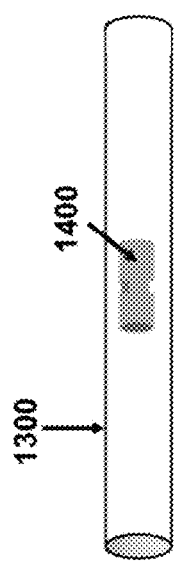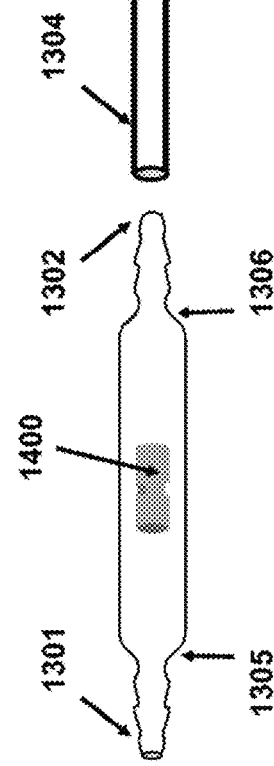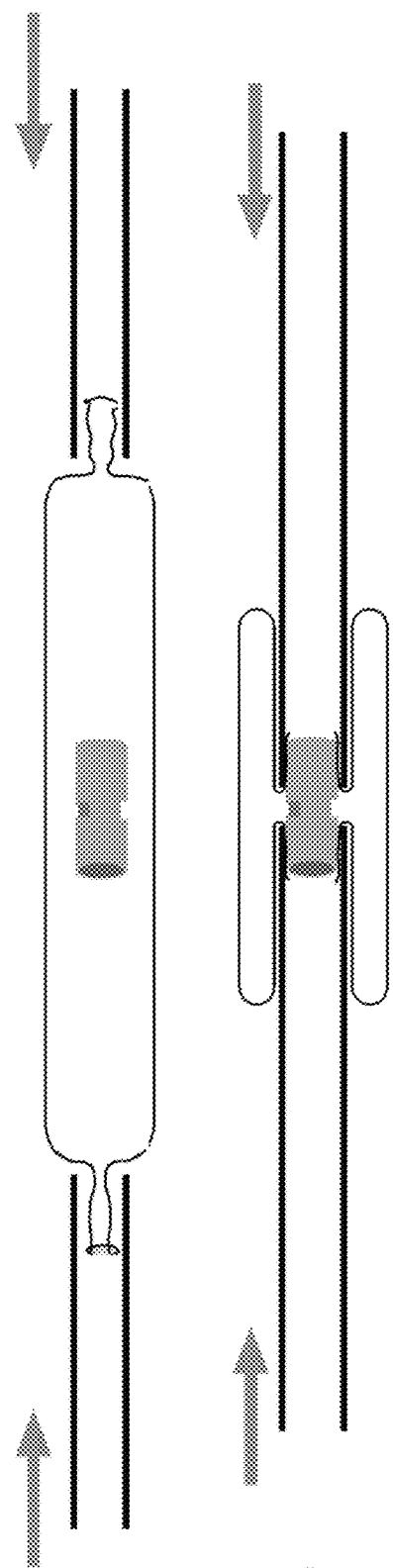
FIG. 14A  FIG. 14B  FIG. 14C  FIG. 14D

METHODS FOR CONSTRUCTION OF MEDICAL DEVICES CONTAINING TOROIDAL BALLOONS

RELATED APPLICATION

This application claims the benefit of provisional application 62/659,756 filed Apr. 19, 2018.

BACKGROUND OF THE INVENTION

Field of Invention

The present invention generally relates to the construction of medical devices, more particularly to medical devices using a rotating toroidal balloon.

Discussion of Prior Art

Medical balloons are ubiquitous in the surgical treatment of patients. These balloons are primarily cylindrical in shape with gathered or tapered ends and used for dilation of a space within biological tissues by inflation of the balloon. They are inserted in a deflated state, inflated to dilate the biological structure or apply a medical device, then deflated for removal. In general, they are not inserted or removed in their inflated state.

Existing toroidal balloons, which are novel variants of medical balloons, are useful because their donut-shape allows construction of the toroidal balloon around a medical device with the medical device located in the "donut hole." Examples of toroidal balloons in medicine are the retention balloons on a Foley catheter and the cuff on an endotracheal tube. Since the balloons have toroidal geometry, they have an inner channel that allows, for example, drainage of urine through the center of the balloon in the case of a Foley catheter, and movement of air in the case of an endotracheal tube. These traditional toroidal balloons are used in general to dilate a biological structure, fill the space between the medical device and a biological wall or to anchor a medical device within a biological structure. Toroidal balloons for use on these existing medical devices are limited in their utility since, when inflated, the balloons do not allow movement of the medical device.

U.S. Pat. Nos. 8,529,581 and 8,343,170 to Massicotte et al. created a version of a toroidal balloon that adds functionality by allowing movement of a medical device through the toroidal balloon's inner channel by rotation of the toroidal balloon. Inflation of the toroidal balloon allows movement of a medical device through biological tissue where the balloon's outside wall is not dragged against the opposing biological wall, rather rolls over the biological wall. This rolling motion of the balloon allows the medical device or an unwanted structure to be moved through a biological space with minimal friction and without contact with the biological wall.

Medical balloons may be constructed from biocompatible polymers such as (but not limited to) urethanes, nylon and other polyamides, polyvinyl chloride (PVC), polyethylene terephthalate (PET). These materials are often extruded into a tube, then the tube is blow-molded into a balloon. This manufacturing process is commonly used in the medical balloon industry. Also, medical balloons may be dipped onto mandrels then cured, or casted by molding (which are common manufacturing techniques for elastomers such as latex rubber and silicone). There exist both open and proprietary techniques for affixing or incorporating the balloons onto catheters or other medical devices. The construction materials, specifications and balloon construction techniques are determined by the devices' function.

In medical devices containing common and simple cylindrical dilating balloons as well as non-rotating toroidal balloons, the balloons are typically constructed from materials different in composition from the associated medical device. The balloons are constructed separately then later attached to the medical device. These balloons function by simple inflation then deflation, and they do not rotate as part of their function. Rotating toroidal balloons may be attached to the medical device using these existing techniques for simple cylindrical balloons but configured in a fashion to allow a toroidal configuration with rotational characteristics.

As with other medical balloons, the rotating toroidal balloon as described in U.S. Pat. Nos. 8,529,581 and 8,343,170 to Massicotte et al. may be created by standard manufacturing techniques such as extrusion and blow-molding, dip molding and micro-extrusion. Also, these rolling toroidal balloons may be attached to the medical device using standard techniques such as, but not limited to, chemical or heat bonding.

FIGS. 1A-E demonstrate the traditional construction of a blow-molded balloon (101) from an extruded catheter (100). In this standard technique, a long tube is extruded then inserted into a mold (102). The tube within the mold is seen in FIG. 1C. According to standard methodology, the complex shown in FIG. 1C is heated and the tube (100) is inflated to the shape of the mold (102) as shown in FIG. 1D. The blow-molded balloon (101) is removed from the mold. But this balloon (101) shown in FIG. 1E may be the basis for a method of construction of a rotating toroidal balloon.

The standard existing technique for construction of cylindrical medical balloon is summarized in FIGS. 2A-C. The blow molded balloon (201), similar to the one shown in FIG. 1E, is then attached at each end of the balloon's ends to a separate medical device. In the example in FIGS. 2A-C, the medical device is a fenestrated catheter (202) where the fenestration (203) is a port for inflation of the cylindrical balloon. The cylindrical balloon (201) is attached to the catheter (202) using chemical or other bonding techniques at each end (204). Attachment of the cylindrical balloon (201) to a separate medical device requires extra production steps, moreover, balloon materials are often different than materials used for construction of the associated medical device. Once the balloon (201) is attached to the fenestrated catheter (202), it is inflated through the enclosed port (203).

Toroidal balloons capable of rotation, such as those described in U.S. Pat. Nos. 8,529,581 and 8,343,170 to Massicotte et al., are novel in the medical world and optimized construction techniques for constructing such balloons have not been established in prior art. This invention describes such an optimal construction.

Whatever the precise merits, features, and advantages of the above cited references, none of them achieves or fulfills the purposes of the present invention.

SUMMARY OF THE INVENTION

In one embodiment, the present invention provides a method for constructing a toroidal balloon as part of a medical device from an extruded tube, the extruded tube having, in order, a first, second and third segment, the method comprising the steps of: (a) inserting a portion of the extruded tube in a mold cavity, the portion corresponding to the second segment, the first and third segments remaining external to the mold cavity; (b) raising a temperature within the mold cavity and inflating the second segment of the extruded tube so it conforms to a cylindrical shape of the mold cavity; (c) advancing the third segment of the extruded tube in a direction of the central axis of the second segment that is inflated in (b) and towards the first segment, the advancing done until the second segment forms a toroidal configuration surrounding the third segment; and (d) sealing the first and third segments.

In another embodiment, the present invention provides a method for constructing a toroidal balloon as part of a medical device from an extruded tube, the extruded tube having, in order, a first and a second segment the method comprising the steps of: (a) inserting the first segment of the extruded tube in a mold cavity, the second segment remaining external to the mold cavity; (b) raising a temperature within the mold cavity and inflating the first segment of the extruded tube so it conforms to a cylindrical shape of the mold cavity; (c) removing the first segment that is inflated in (b) outside the mold cavity; (d) wrapping over a free end of the first segment over a portion of itself to form a toroidal balloon; (e) creating a port near an end of the second segment that is closest to the first segment; (f) attaching the free end wrapped over in (d) to the second segment wherein after the attaching, the port is positioned to aid in inflation/deflation of the toroidal balloon; (g) inflating the toroidal balloon via the port; (h) rotating the toroidal balloon over itself to cover the second segment; and (i) sealing both ends of the second segment.

In yet another embodiment, the present invention provides a method for constructing a toroidal balloon as part of a medical device, the method comprising the steps of: (a) inserting an extruded tube within a protective tube, the extruded tube having a first end and a second end disposed outside the protective tube; (b) attaching the first end of the extruded tube to a first segment of the medical device; (c) attaching the second end of the extruded tube to a second segment of the medical device; (d) inflating the extruded tube within the protective tube so it conforms to a cylindrical shape of the protective tube; (e) advancing the first and second segments relative to each other to decrease a distance between the first and second segments, the advancing done until the extruded tube forms a toroidal configuration surrounding both the first and second segment of the medical device; and (f) sealing open ends of the first and second segments.

In another embodiment, the present invention provides a method for constructing a toroidal balloon as part of a medical device, the method comprising the steps of: (a) forming a cylindrical medical balloon having a first and second end; (b) collapsing a first portion near the first end of the cylindrical medical balloon and collapsing a second portion near the second end of the cylindrical medical balloon, the remainder portion of the cylindrical medical balloon maintaining its cylindrical shape; (c) inserting the first portion to an interior of a first segment of the medical device and inserting the second portion to another interior of a second segment of the medical device; (d) advancing the first and second segments relative to each other to decrease a distance between the first and second segments, the advancing done until the remainder portion of the cylindrical medical balloon forms a toroidal configuration surrounding both the first and second segment of the medical device; and (e) sealing open ends of the first and second segments.

BRIEF DESCRIPTION OF THE DRAWINGS

FIGS. 1A-1E depict the traditional construction of a blow-molded balloon from an extruded catheter.

FIGS. 2A-2C depict standard existing technique for construction of cylindrical medical balloon.

FIG. 3A-3C illustrate rotation of the toroidal balloon over a distance without the outer walls of the balloon moving against the opposing biological surface.

FIGS. 4A-4F depict one example of the present invention's method for constructing a toroidal balloon that is part of a medical device, where the toroidal balloon and the medical device are contiguous.

FIGS. 5A-5E depict another example of the present invention's method for constructing a toroidal balloon that is part of a medical device, where the toroidal balloon and the medical device are contiguous, and the toroidal balloon is formed within a mold.

FIG. 5F depicts a flow chart outlining the steps associated with one embodiment of the present invention for forming the toroidal balloon shown in FIG. 4D and FIG. 5E.

FIGS. 6A-6G depict another example of the present invention's method for constructing a toroidal balloon that is part of a medical device, where the toroidal balloon and the medical device are contiguous and are sealed at one end via a fenestrated bridge and at another end via an injection syringe.

FIGS. 7A-D depict an example of how the toroidal balloon constructed as per the teachings of the present invention may be used for the extraction of ureteral stones.

FIGS. 8A-8D illustrate how the device shown in FIGS. 7A-7D for extraction of ureteral stones is used without dragging the balloon against the ureter.

FIGS. 9A-9I illustrate another variation for constructing a toroidal balloon wherein free ends of the balloon are wrapped over itself to create the toroidal balloon.

FIGS. 10A-10F illustrate another variation for constructing a toroidal balloon by attaching a cylindrical balloon, internally, to different segments of a medical device where, after inflation, the different segments are moved relative to each other to form the toroidal balloon.

FIGS. 11A-11G illustrate another variation for constructing a toroidal balloon by attaching a cylindrical balloon, externally, to different segments of a medical device where, after inflation, the different segments are moved relative to each other to form the toroidal balloon.

FIGS. 14A-14D illustrate another embodiment of the present invention that is similar to what is shown in FIGS. 13A-13D but with a fenestrated bridge that is contained within the balloon.

DESCRIPTION OF THE PREFERRED EMBODIMENTS

Figure 9J:
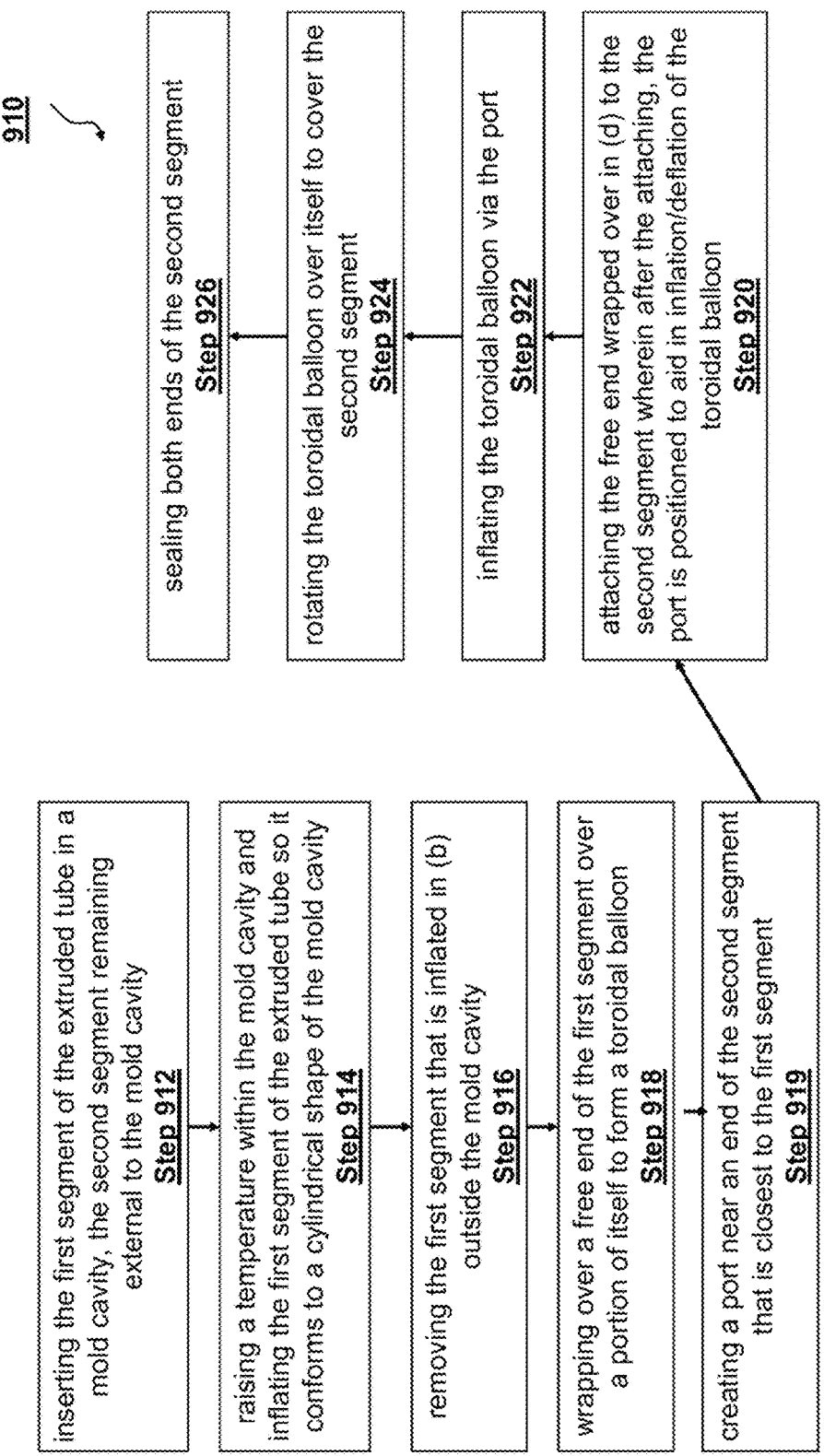
FIG. 9J depicts a flow chart outlining the steps associated with one embodiment of the present invention for forming the toroidal balloon shown in FIG. 9I.

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The geometry of a toroidal balloon requires that a traditional cylindrical balloon to be rotated internally into itself and the ends of the cylinder be placed in close proximity for maximal balloon rotation and to allow an entrance port for inflation of the balloon and/or attachment to an associated medical device. The present invention describes novel techniques for the creation of rotating toroidal balloons.

A toroidal balloon as described by Massicotte et al. in U.S. Pat. Nos. 8,529,581 and 8,343,170 is an improvement over the existing cylindrical balloons since toroidal balloons are elongated donut-shaped balloons that permit rotational movement. The existing cylindrical balloons (FIG. 2C) are attached to the device at each end (204) and therefore have no rotational capability. A toroidal balloon (305) is wrapped into itself internally to create the donut shape (FIGS. 3A-C), and so the attachments to the medical device are near each other (304) allowing just enough distance for the catheter's fenestration (303) necessary for inflation of the toroidal balloon (305). This narrow attachment (304) of the toroidal balloon (305) to the inflation catheter (302) allows rotation of the toroidal balloon over a long distance (FIGS. 3A-C), without the outer walls of the balloon moving against the opposing biological surface (306).

The present invention describes efficient construction techniques of a toroidal balloon from a standard blow molded cylindrical balloon as seen in FIG. 1E. The present invention's optimized manufacturing techniques allow for the extruded tube (100) to be formulated as part of the medical device itself, in contrast to a simple extruded stock tube used to blow mold the cylindrical balloon, only to discard the extra segment of the stock extruded tube. And since the balloon is blown from a segment of the device itself, the connection between the balloon and the device is an inherent part of its construction and no bonding will be necessary between the inflatable balloon and the medical device. The process is demonstrated in FIGS. 4A through 6G.

In one method (FIGS. 4A through 6G), a catheter is extruded and then a portion of the extruded catheter is blow-molded per routine. In this novel case, however, the extruded catheter is designed in such a way to be a substantial part of the medical device. When a segment of the extruded medical device itself is blow-molded into a balloon, no bonding is necessary at either one or two of the balloon's ends since the balloon and the catheter are contiguous. The catheter end(s) located at the junction of the of the blown balloon are moved through the internal aspect of the balloon to close contiguous proximity of each other, inverting the balloon and creating the two-layered rotating toroidal balloon. A separate piece is added to bridge and maintain the gap between the catheter/balloon junction.

FIGS. 4A-F contain simple diagrams of the novel method for construction of toroidal balloons. Note that there are no medical devices with rotating toroidal balloons and so this technique for construction is novel. FIG. 4A is a blow-molded balloon such as the one shown in FIG. 1E. The extruded tube is designed with particular specifications in materials and dimensions so that the balloon segment (402) of the medical device and the non-blow-molded segment (403) of the medical device have qualities appropriate for the device's application. The importance of the extruded medical device (403) being of particular specifications will become evident in the example below in FIGS. 7A-D where this segment (403) is the sheath in which the ureteroscope is inserted as well as the inflation tube. While keeping the balloon inflated, the extruded segment is advanced into the center of the balloon as in FIG. 4B, forming a toroidal configuration as in FIG. 4C. To connect the ends of the balloon and to create the continuous medical device (in this case, a catheter for inflation), a fenestrated bridge (400) is inserted to bridge the gap between the balloon/extruded catheter junctions (401) as demonstrated in FIGS. 4D-F.

This fenestrated bridge (400) which provides structural integrity to maintain the toroidal balloon's shape will be bonded to each extruded segment yet will allow the toroidal balloon to be inflated through the fenestration. The bridge has other beneficial properties related to the medical device's use that will be discussed shortly in this text.

FIGS. 5A through FIG. 6G show a slightly more detailed demonstration of the toroidal medical device's construction including more details on the fenestrated bridge (400). The carefully designed extruded tube (500) which is the backbone of the device will be constructed with such materials and dimensions necessary for its function as part of the medical device both in the region to be blow molded and the region that is a substantial part of the medical device itself. The medical device (500) is inserted into the mold (102) as in FIG. 5B. In FIG. 5C, the balloon is blow molded then inverted into itself as in FIG. 5D, creating a toroidal balloon (FIG. 5E). This configures the balloon (FIGS. 5E, 6A and 6B) for insertion of the fenestrated bridge (400) as shown in FIG. 6C. FIG. 6G is a magnified view of the fenestrated bridge. The bridge (400) is configured for a specific ureteroscope (for example) thereby creating a seal at (603) with the ureteroscope in the example discussed in FIGS. 7A-D. The shaded bands (604) show the region where the bridge is attached to the inner channel of the extruded medical device. In FIG. 6D, the fenestrated bridge (400) is then bonded to the inner aspect of the extruded catheter. Note that the bridge (400) is a generic structure that can be constructed with different specifications according to its use and the device with which it is to be paired.

FIG. 6E shows the toroidal balloon in a deflated state. The toroidal balloon (600) can then be inflated by injection syringe (601) or other inflation mechanism of fluid or air through the catheter as in FIG. 6F, through the fenestrations bridge (400) and into the toroidal balloon.

The toroidal balloon catheter shown in FIG. 7A is similar to the balloon in FIG. 6E. This toroidal balloon configuration provides the basis for a device (FIG. 7B) used for extraction of ureteral stones as demonstrated in the example by Massicotte et al. in U.S. Pat. Nos. 8,529,581 and 8,343,170. The medical device in FIG. 7B has a longer toroidal balloon and an attachment (701) that provides both a water tight seal with a compression ring (702) similar to a Tuohy-Borst Adaptor (Cook® Medical, Order number TBA-6) and also contains an inflation valve (703).

Using the toroidal balloon device (FIG. 7B) for extraction of ureteral stones as an example, a ureteroscope (FIG. 7C) is inserted into the toroidal device (FIG. 7B). FIG. 7D shows the complex. The fenestrated bridge (700) is tight at the tip of the ureteroscope creating a distal seal (704) at the tip of the ureteroscope and a seal at (705) by tightening the adaptor (702) and compressing a gasket ring. There is now a watertight space between the walls of the medical device and the ureteroscope and the toroidal balloon can be inflated at (703). This construction, where the balloon is inflated outside of the ureteroscope but within the medical device, minimizes the diameter of the toroidal device/ureteroscope complex shown in FIG. 7D.

FIG. 5F depicts a flow chart depicting one embodiment (corresponding to the steps described previously with regards to FIGS. 5A-E) to construct a toroidal balloon as part of a medical device from an extruded tube, the extruded tube having, in order, a first, second and third segment, the method 510 of this embodiment comprising the steps of: (a) inserting a portion of the extruded tube in a mold cavity, the portion corresponding to the second segment, the first and third segments remaining external to the mold cavity—step 512; (b) raising a temperature within the mold cavity and inflating the second segment of the extruded tube so it conforms to a cylindrical shape of the mold cavity—step 514; (c) advancing the third segment of the extruded tube in a direction of the central axis of the second segment that is inflated in (b) and towards the first segment, the advancing done until the second segment forms a toroidal configuration surrounding the third segment—step 516; and (d) sealing the first and third segments—step 518.

To demonstrate the function of this example, as shown in the prior art of Massicotte et al. in U.S. Pat. Nos. 8,529,581 and 8,343,170, refer to FIGS. 8A-D. FIG. 8A shows the ureteroscope equipped with the toroidal balloon device within a ureter. The toroidal balloon (801) is inflated in FIG. 8B with a syringe (802) in this example. With the toroidal balloon in an inflated state, traction on the ureteroscope in FIG. 8C causes the balloon to rotate inwardly. It is noteworthy that the outside wall of the balloon is not dragged against the opposing biological wall (ureter in this case) and the toroidal balloon is removed by internal rotation.

In one embodiment, a toroidal balloon (900) is constructed by extruding a segment of a medical device then blow-molding a portion of the device to be used for its toroidal balloon. This technique forgoes the need to attach a separate balloon to a medical device which save steps in construction and also does not require adhesives or bands that may add to the device's diameter at the attachment sites. In the above example, both ends of the balloon are contiguous with the body of the medical device (401), and the toroidal balloon is created by bringing the balloon junctions near to each other within the toroidal balloon and installing a bridge (400) between the two balloon ends (401). It is noted that the construction of a toroidal balloon where only one end of the balloon is contiguous with the medical device is also within the scope of the present invention.

This variation is shown in FIGS. 9A-I where the balloon's free end (901) is wrapped over itself (FIGS. 9C, 9D and 9E) then attached (901) using an adhesive, a band or other standard technique, similar to FIGS. 2A-C, Item (204). The toroidal balloon is then rotated over itself as in FIG. 9H, creating the toroidal balloon (FIG. 9I). Accordingly, in FIGS. 9A-I, the balloon is created by standard blow molding of a segment of the extruded medical device catheter, but the distal end is folder over the balloon externally and attached just proximal to the catheter/balloon junction to create the two-layer toroidal balloon. It should be noted that while not explicitly shown in FIG. 9F, before the free end of the wrapped balloon is attached, a small port 902 is made at an end of the extruded device as shown in FIG. 9G, just proximal to the catheter/balloon junction, to later serve as the balloon's inflation port. In this case, one end of the toroidal balloon is contiguous with the medical device and the other is bonded to the medical device per standard technique.

FIG. 9J depicts a flowchart showing the steps of a method 910 for constructing a toroidal balloon as part of a medical device from an extruded tube as per the teachings of one embodiment of the present invention, wherein the extruded tube having, in order, a first and a second segment, the method comprising the steps of: (a) inserting the first segment of the extruded tube in a mold cavity, the second segment remaining external to the mold cavity—step 912; (b) raising a temperature within the mold cavity and inflating the first segment of the extruded tube so it conforms to a cylindrical shape of the mold cavity—step 914; (c) removing the first segment that is inflated in (b) outside the mold cavity—step 916; (d) wrapping over a free end of the first segment over a portion of itself to form a toroidal balloon—step 918; (e) creating a port near an end of the second segment that is closest to the first segment—step 919; (f) attaching the free end wrapped over in (d) to the second segment wherein after the attaching, the port is positioned to aid in inflation/deflation of the toroidal balloon—step 920; (g) inflating the toroidal balloon via the port—step 922; (h) rotating the toroidal balloon over itself to cover the second segment—step 924; and (i) sealing both ends of the second segment—step 926.

It is worth emphasizing again that rotating toroidal balloons on medical devices, such as those described under the prior art of Massicotte et al. in U.S. Pat. Nos. 8,529,581 and 8,343,170, are novel and, as a result, there is no existing intellectual property for the construction of these rotating toroidal balloons. Other manufacturing techniques for construction of rotating toroidal balloon are also claimed here. In the techniques described in FIGS. 10A through FIG. 12D, the balloon is constructed separately from the medical device (in contrast to the manufacturing techniques claimed above) then bonded to the device or manipulated by a construction guide then rolled into a toroidal configuration.

One of such techniques is described in FIGS. 10A-F. A cylindrical medical balloon (1000) is made using the standard blow or dip molded or micro-extrusion technique. Each end of the balloon (1001, 1002) is attached to a different segment of the medical device (1003, 1004) along the device's INTERNAL lumina using standard bonding techniques (FIG. 10B). The balloon (1000) is inflated within a protective tube (1005) to precisely control to balloon's (1000) inflated volume and dimensions. After inflation of the balloon (FIG. 10C), the two junctions are then brought in proximity to each other (FIGS. 10D, 10E and 10F) through the INTERNAL aspect of the balloon (1000) while folding the balloon over the medical device and creating a two-layered toroidal balloon.

In another technique (FIGS. 11A-G), a cylindrical medical balloon (1100) is made using the standard blow or dip molded or micro-extrusion technique. Each end of the balloon (1101, 1102) is attached (FIG. 11B) to a different segment of the medical device (1103, 1104) along the device's external surfaces using standard bonding techniques. The balloon (1000) is inflated within a protective tube (1005) to precisely control to balloon's (1000) inflated volume and dimensions. After inflation of the balloon (FIG. 11C), the two junctions are then brought in proximity to each other (FIGS. 11D-F) through the INTERNAL aspect of the balloon (1100) while folding the balloon over the medical device and creating a two-layered toroidal balloon (FIG. 11G).

Of note, the final step in creation of the toroidal balloons in FIGS. 10A-F and FIGS. 11A-G requires the internal addition of a fenestrated bridge. This fenestrated bridge may be of any length but always spans the gap between the balloon ends. One example of such a bridge is already seen in FIGS. 6A-G.

Figure 11H:
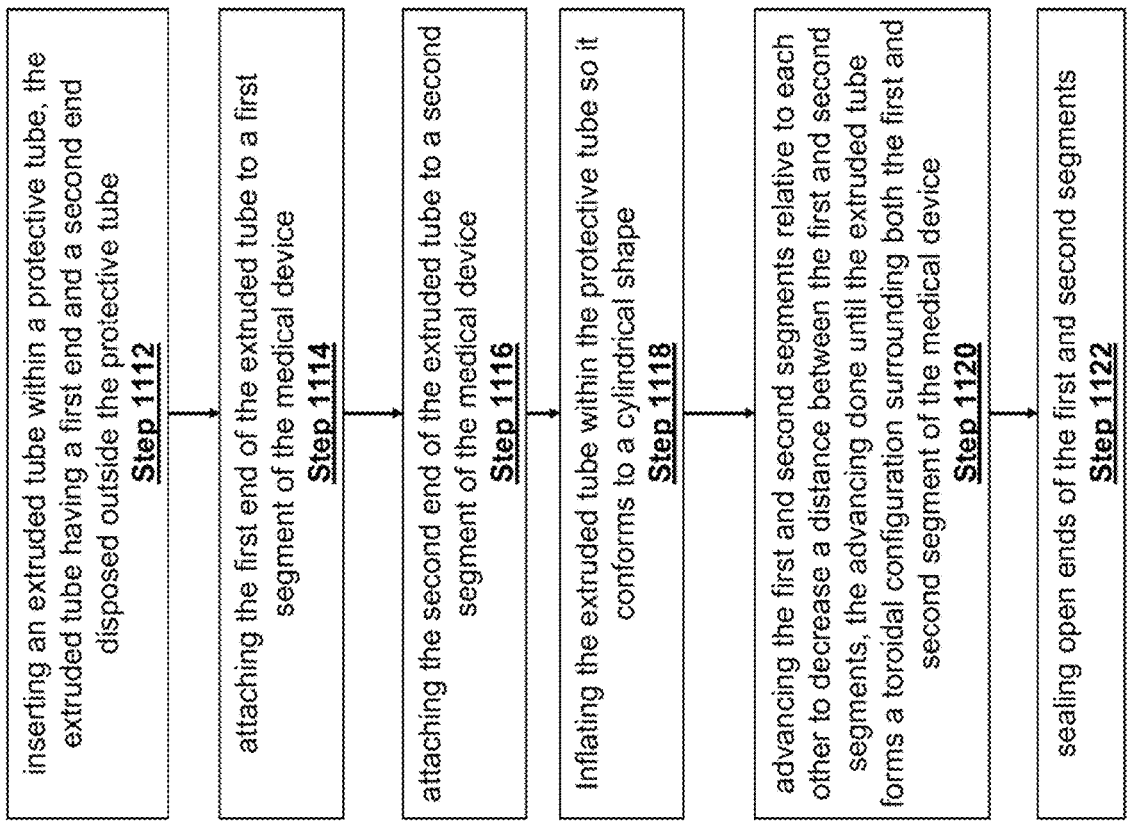
FIG. 11H depicts a flow chart outlining the steps associated with one embodiment of the present invention for forming the toroidal balloon shown in FIG. 10F or FIG. 11F.

FIG. 11H depicts a flowchart showing the steps of a method 1110 for constructing a toroidal balloon as part of a medical device as per the teachings of one embodiment of the present invention, wherein the method comprises the steps of: (a) inserting an extruded tube within a protective tube, the extruded tube having a first end and a second end disposed outside the protective tube—step 1112; (b) attaching the first end of the extruded tube to a first segment of the medical device—step 1114; (c) attaching the second end of the extruded tube to a second segment of the medical device—step 1116; (d) inflating the extruded tube within the protective tube so it conforms to a cylindrical shape—step 1118; (e) advancing the first and second segments relative to each other to decrease a distance between the first and second segments, the advancing done until the extruded tube forms a toroidal configuration surrounding both the first and second segment of the medical device—step 1120; and (f) sealing open ends of the first and second segments—step 1122.

Another example is seen in FIGS. 12A-D. In the technique depicted in FIGS. 12A-D, each end of a balloon may be collapsed relative to the balloon and the two junctions are brought in proximity through the internal aspect of the balloon using cylindrical guides. A generic medical device (1200) that contains at least one lumen for inflation is inserted into one of the toroidal balloons constructed in FIGS. 10A-F or FIGS. 11A-G to provide a fenestrated bridge over the gap (1202) between balloon ends. The two components (1200, 1201) are fused, creating a new toroidal balloon device (1203). In this example, the toroidal device (1203) is connected to a syringe (1205) which inflates the toroidal balloon (1204). The are many potential variations in lengths of the balloon, the medical device and the bridge.

Figure 12A:
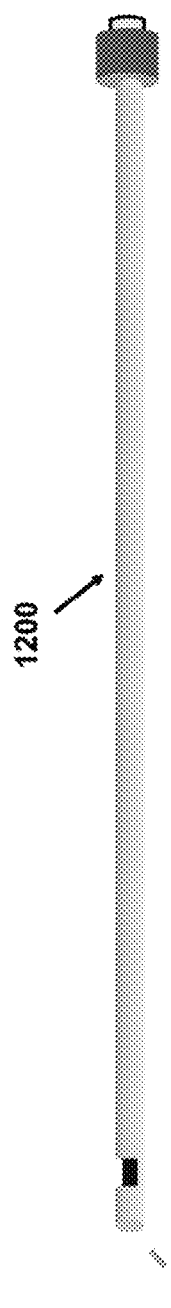
FIGS. 12A-12D illustrate another embodiment, where two components (a generic medical device and a tube with the toroidal balloon) are fused together to create a new toroidal balloon device.
Figure 12B:
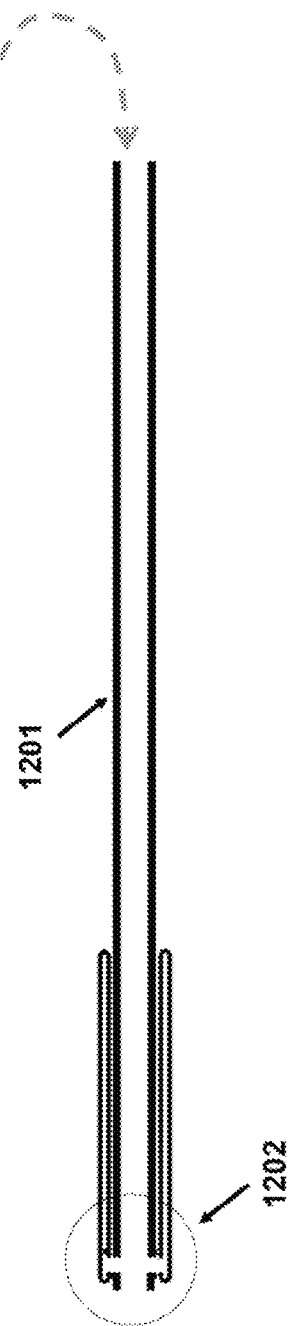
Figure 12C:
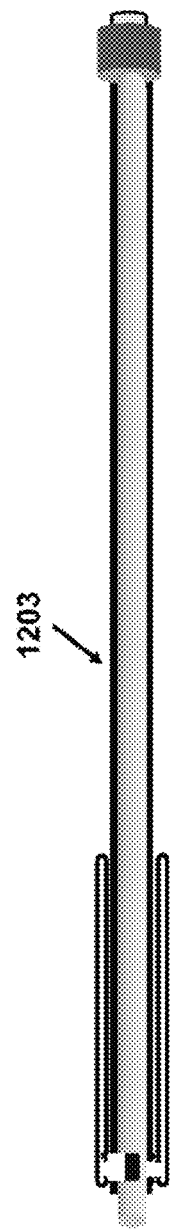
Figure 12D:
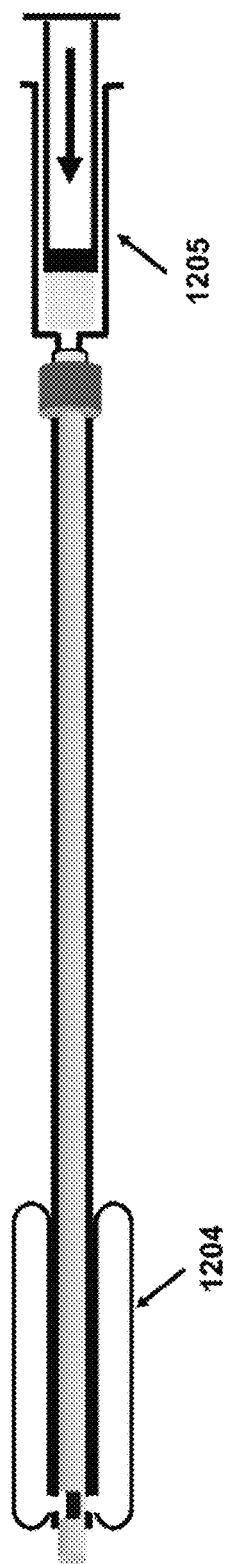
Figures 13A, 13B, 13C, 13D:
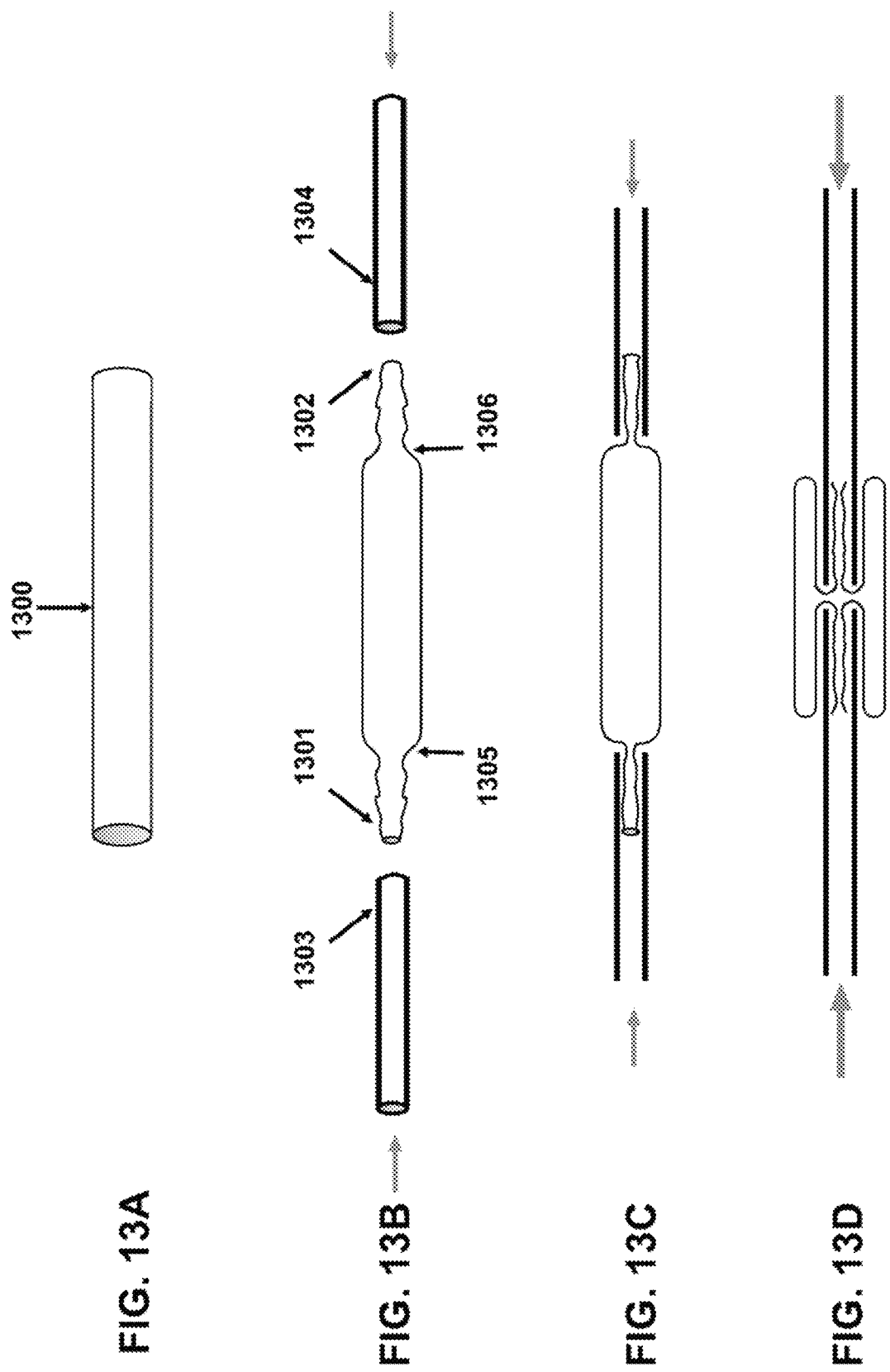
FIGS. 13A-13D illustrate another embodiment of the present invention where a portion of each end of a cylindrical balloon is collapsed to be inserted into different segments of a medical device, wherein the different segments are moved relative to each other to form the toroidal balloon.

In another technique (FIGS. 13A-D), a cylindrical medical balloon (1300) is made using the standard blow or dip molding or micro-extrusion technique. The technique (FIGS. 13A-D) is similar to the technique described in FIGS. 10A-F where the toroidal balloon is created by folding the balloon's ends internally, however, the internal folding in FIGS. 13A-D is done on an extruded or dipped balloon in its resting (uninflated) state rather that in an inflated state as in technique described in FIG. 10A-F. Each end of a balloon (1301, 1302) is collapsed relative to the balloon. The balloon's ends (1301, 1302) may be simply collapsed and gathered to fit within the manufacturing guides (1303,1304), or by other common technique. In FIG. 12B, the collapsed balloon segments (1301, 1302) are inserted into cylindrical manufacturing guides (1303, 1304) as seen in FIG. 12C. The toroidal configuration is created by inversion of the cylindrical balloon (1300) internally by bringing the manufacturing guides in opposition. Thus, the two junctions (1305, 1306) are brought in proximity (FIG. 12B) through the internal aspect of the balloon (1300) using cylindrical guides (1303, 1304), creating the toroidal balloon. FIGS. 14A-D show a similar technique to FIGS. 13A-D, but in another technique, a fenestrated bridge (1400) is contained within the balloon prior to rolling it.

Figure 15:
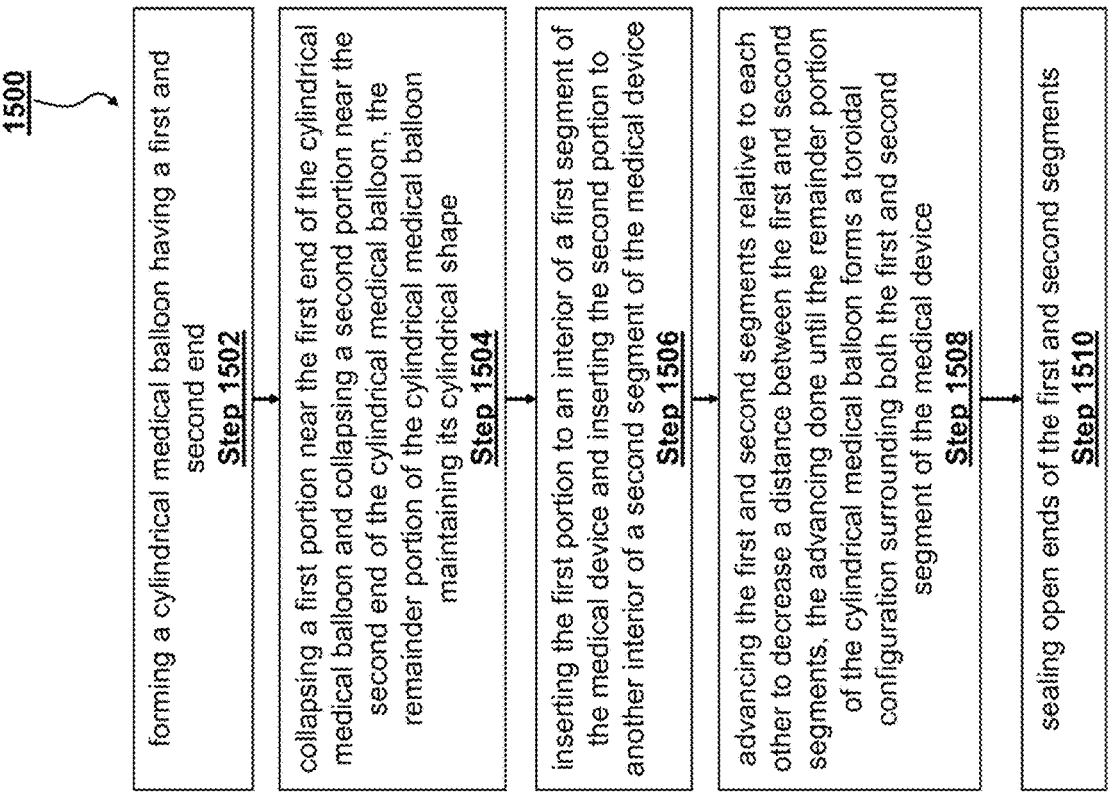
FIG. 15 depicts a flow chart outlining the steps associated with one embodiment of the present invention for forming the toroidal balloons shown in FIG. 13D or 14D.

FIG. 15 depicts a flowchart showing the steps of a method 1500 for constructing a toroidal balloon as part of a medical device as per the teachings of one embodiment of the present invention, wherein the method for constructing a toroidal balloon as part of a medical device comprises the steps of: (a) forming a cylindrical medical balloon having a first and second end—step 1502; (b) collapsing a first portion near the first end of the cylindrical medical balloon and collapsing a second portion near the second end of the cylindrical medical balloon, the remainder portion of the cylindrical medical balloon maintaining its cylindrical shape—step 1504; (c) inserting the first portion to an interior of a first segment of the medical device and inserting the second portion to another interior of a second segment of the medical device—step 1506; (d) advancing the first and second segments relative to each other to decrease a distance between the first and second segments, the advancing done until the remainder portion of the cylindrical medical balloon forms a toroidal configuration surrounding both the first and second segment of the medical device—step 1508; and (e) sealing open ends of the first and second segments—step 1510.

CONCLUSION

A method has been shown in the above embodiments for the effective construction of medical devices containing toroidal balloons. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:

1. A method for constructing a toroidal balloon as part of a medical device from an extruded tube, the extruded tube having, in order, a first, second and third segment, the method comprising the steps of:
   a. inserting a portion of the extruded tube in a mold cavity, the portion corresponding to the second segment, the first and third segments remaining external to the mold cavity;
   b. raising a temperature within the mold cavity and inflating the second segment of the extruded tube so it conforms to a cylindrical shape of the mold cavity;
   c. forming a toroidal configuration inside the mold cavity where the inflating in (b) was done by advancing the third segment of the extruded tube into the mold cavity and in a direction of the central axis of the second segment that is inflated in (b) and towards the first segment, the advancing done until the second segment forms the toroidal configuration surrounding the third segment; and
   d. sealing the first and third segments.

2. The method of claim 1, wherein a fenestrated bridge is used to seal the first segment.

3. The method of claim 1, wherein a Tuohy Borst adaptor is used to seal the third segment.

4. The method of claim 1, wherein the medical device is a catheter.

5. The method of claim 1, wherein the extruded tube is made from an elastomer.

6. The method of claim 1, wherein the extruded tube is made from a biocompatible polymer.

\* \* \* \* \*